United States Patent
Pazenok et al.

(10) Patent No.: US 9,765,033 B2
(45) Date of Patent: Sep. 19, 2017

(54) METHOD FOR THE PRODUCTION OF 3,5-BIS(FLUOROALKYL)PYRAZOLE DERIVATIVES

(71) Applicant: BAYER CROPSCIENCE AKTIENGESELLSCHAFT, Monheim am Rhein (DE)

(72) Inventors: Sergii Pazenok, Solingen (DE); Norbert Lui, Odenthal (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 14/892,280

(22) PCT Filed: May 19, 2014

(86) PCT No.: PCT/EP2014/060241
§ 371 (c)(1),
(2) Date: Nov. 19, 2015

(87) PCT Pub. No.: WO2014/187774
PCT Pub. Date: Nov. 27, 2014

(65) Prior Publication Data
US 2016/0122304 A1    May 5, 2016

(30) Foreign Application Priority Data
May 22, 2013 (EP) .................................... 13168741

(51) Int. Cl.
*C07D 231/12* (2006.01)
*C07D 231/14* (2006.01)
*C07C 251/80* (2006.01)
*C07C 251/88* (2006.01)

(52) U.S. Cl.
CPC .......... *C07D 231/12* (2013.01); *C07C 251/80* (2013.01); *C07C 251/88* (2013.01); *C07D 231/14* (2013.01)

(58) Field of Classification Search
None
See application file for complete search history.

(56) References Cited

U.S. PATENT DOCUMENTS

| | | |
|---|---|---|
| 2,969,374 A | 1/1961 | Bernard et al. |
| 7,329,633 B2 | 2/2008 | Dunkel et al. |
| 7,358,387 B2 | 4/2008 | Lantzsch et al. |
| 7,521,397 B2 | 4/2009 | Dunkel et al. |
| 7,939,673 B2 | 5/2011 | Pazenok et al. |
| 8,350,053 B2 | 1/2013 | Pazenok et al. |
| 8,592,605 B2 | 11/2013 | Pazenok et al. |
| 8,629,288 B2 | 1/2014 | Pazenok et al. |
| 8,759,527 B2 | 6/2014 | Tsuchiya et al. |
| 9,006,266 B2 | 4/2015 | Tsuchiya et al. |
| 9,150,565 B2 | 10/2015 | Tsuchiya et al. |
| 9,518,025 B2 * | 12/2016 | Pazenok .............. C07D 231/12 |
| 2003/0096990 A1 | 5/2003 | Read et al. |
| 2009/0326242 A1* | 12/2009 | Pazenok .............. C07D 231/14 548/374.1 |
| 2015/0011779 A1 | 1/2015 | Pazenok et al. |
| 2015/0175598 A1 | 6/2015 | Tsuchiya et al. |
| 2015/0239846 A1 | 8/2015 | Pazenok et al. |

FOREIGN PATENT DOCUMENTS

| | | |
|---|---|---|
| WO | 03070705 A1 | 8/2003 |
| WO | 2005042468 A1 | 5/2005 |
| WO | 2008013925 A2 | 1/2008 |
| WO | 2008022777 A2 | 2/2008 |
| WO | 2009106230 A2 | 9/2009 |
| WO | 2009112157 A1 | 9/2009 |
| WO | 2012025557 A1 | 3/2012 |
| WO | 2013113829 A1 | 8/2013 |
| WO | 2014023667 A1 | 2/2014 |

OTHER PUBLICATIONS

Patani et al. (Chemical Reviews, 1996, vol. 96, 3147-3176).*
International Search Report from corresponding PCT/EP2014/060241, mailed Jul. 15, 2014.
Braun et al., "2-Diphenylacetyl-1,3-indandione 1-Hydrazone—A New Reagent for Carbonyl Compounds", Journal of the American Chemical Society, Bd. 90, Nr. 12, 1958, pp. 3048-3050, XP055083349.
Maspero et al., "Filling the gap: Chemistry of 3,5-bis(trifluoromethyl)-I-pyrazoles", Journal of Fluorine Chemistry, Bd. 139, Apr. 11, 2012, pp. 53-57, XP028423590.
Kurihara et al., "Physicochemical Properties of Isomeric Azines of 3-Acetyl-4-hydroxy-2-methoxy-4-phenylcrotonic Acid Lactones", Chemical & Pharmaceutical Bulletin, Bd. 31, Nr. 3, 1983, pp. 912-918, XP055083420.
Weigert et al., "Hexafluoroacetone hydrazone chemistry", Journal of Fluorine Chemistry, Bd. I, Nr. 4, 1972, pp. 445-462, XP026635635.
Pashkevich et al., Zhurnal Vsesoyuznogo Khimicheskogo Obshchestva named after D. I. Mendeleeva, 1981, 26(1), pp. 105-107.

* cited by examiner

*Primary Examiner* — Kamal Saeed
(74) *Attorney, Agent, or Firm* — McBee Moore Woodward & Vanik IP, LLC; Susan McBee; David Woodward

(57) ABSTRACT

The present invention describes a novel method for preparing 3,5-bis(fluoroalkyl)pyrazole derivatives.

14 Claims, No Drawings

METHOD FOR THE PRODUCTION OF 3,5-BIS(FLUOROALKYL)PYRAZOLE DERIVATIVES

CROSS REFERENCE TO RELATED APPLICATIONS

This application is a §371 National Stage Application of PCT/EP2014/060241, filed 19 May 2014, which claims priority to EP 13168741.0, filed 22 May 2013.

BACKGROUND

Field of the Invention

The present invention relates to a novel method for preparing 3,5-bis(fluoroalkyl)pyrazole derivatives.

Description of Related Art

Polyfluoroalkylpyrazolylcarboxylic acid derivatives and 3,5-bis(fluoroalkyl)pyrazoles are important precursors of active fungicidal ingredients (cf. WO 2003/070705, WO 2008/013925, WO 2012/025557).

Monoperfluoroalkylpyrazolecarboxylic acid derivatives are typically prepared by reacting acylated acrylic acid derivatives with hydrazines (cf. WO 2009/112157 and WO 2009/106230). WO 2005/042468 discloses a method for preparing 2-dihaloacyl-3-aminoacrylic esters by reacting acid halides with dialkylaminoacrylic esters and subsequent cyclization thereof with alkyl hydrazines. WO 2008/022777 describes a method for preparing 3-dihalomethylpyrazole-4-carboxylic acid derivatives by reacting α,α-difluoroalkylamines in the presence of Lewis acids with acrylic acid derivatives and subsequent reaction thereof with alkyl hydrazines.

3,5-Bis(fluoroalkyl)pyrazoles are prepared by reacting bisperfluoroalkyldiketones (e.g. 1,1,1,5,5,5-hexafluoroacetylacetone) with hydrazines (cf. Pashkevich et al., Zhurnal Vsesoyuznogo Khimicheskogo Obshchestva named after D. I. Mendeleeva (1981), 26(1), 105-7), in which the yield is only 27-40%. The synthesis of bisperfluoroalkyldiketones by the Claisen reaction of fluoroalkylketones and esters of polyfluoroalkylcarboxylic acids is very complex. Polyfluoroalkylketones comprising a $CH_3$ group (e.g. 1,1-difluoroacetone, 1,1,1-trifluoroacetone) react under strongly basic reaction conditions (NaH, KO$^t$Bu) not only with the ester, but in part with itself (aldol reaction), such that the yields are moderate. In addition, polyfluoroalkyldiketones are often volatile and highly toxic, such that isolation and purification thereof presents additional problems.

In the light of the prior art described above, it is an object of the present invention to provide a method that does not have the aforementioned disadvantages and hence provides a route to 3,5-bis(fluoroalkyl)pyrazole derivatives in high yields.

SUMMARY

The object described above was achieved by a method for preparing 3,5-bis(fluoroalkyl)pyrazole derivatives of the formula (Ia) and (Ib),

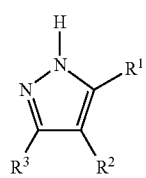

(Ia)

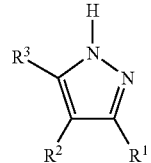

(Ib)

in which $R^1$ and $R^3$ are each independently selected from $C_1$-$C_6$-haloalkyl;

$R^2$ is selected from H, F, Cl, Br, COOH, (C=O)O$R^4$, CN and (C=O)N$R^4R^5$;

$R^4$ and $R^5$ are each independently selected from $C_{1-12}$-alkyl, $C_{3-8}$-cycloalkyl, $C_{6-18}$-aryl, $C_{7-19}$arylalkyl or $C_{7-19}$-alkylaryl or $R^4$ and $R^5$ may form a five- or six-membered ring together with the nitrogen atom to which they are attached;

characterized in that in step (A) fluoroalkyl esters, thioesters or amides of the formula (II),

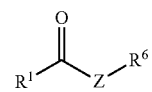

(II)

in which

Z is selected from O, S, N—$R^4$;

$R^4$ is as defined above;

$R^6$ is selected from $C_{1-12}$-alkyl, $C_{3-8}$-cycloalkyl, $C_{6-18}$-aryl, $C_{7-19}$-arylalkyl or $C_{7-19}$-alkylaryl or $R^4$ and $R^6$ may form a five- or six-membered ring together with the nitrogen atom to which they are attached;

$R^1$ is as defined above;

are reacted with compounds of the formula (III),

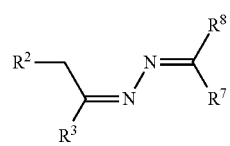

(III)

in which the residues $R^2$, $R^3$, $R^4$ and $R^5$ are as defined above, $R^7$ and $R^8$ are each independently selected from H, $C_{1-12}$-alkyl, $C_{3-8}$-cycloalkyl, $C_{6-18}$-aryl, $C_{7-19}$-arylalkyl or $C_{7-19}$-alkylaryl or $R^7$ and $R^8$ may form a four-, five- or six-membered ring;

in the presence of a base to give compounds of the formula (IV),

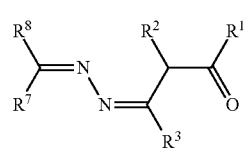

(IV)

where $R^1$, $R^2$, $R^3$, $R^7$ and $R^8$ are as defined above, and which are then cyclized in step (B) in the presence of an acid to give compounds of the formula (Ia) and (Ib).

DETAILED DESCRIPTION OF A PREFERRED EMBODIMENT

Surprisingly, the pyrazoles of the formula (Ia) and (Ib) can be prepared under the inventive conditions with good yields and in high purity, which means that the method according to the invention overcomes the abovementioned disadvantages of the preparation methods previously described in the prior art.

Preference is given to a process according to the invention in which the definitions of the residues of the compounds of the formulae (Ia), (Ib), (II), (III) and (IV) are defined as follows:

$R^1$ and $R^3$ are each independently selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl;

$R^2$ is selected from H, Cl, COOH, $COOCH_3$, $COOC_2H_5$, $COOC_3H_7$, CN and $CON(CH_3)_2$, $CONC_3H_7$;

Z is selected from O, S, N—$R^4$;

$R^4$ is selected from methyl, ethyl, n-propyl, isopropyl, n-, sec- and t-butyl, isobutyl, cyclopropyl, cyclobutyl, cyclopentyl, cyclohexyl, phenyl, benzyl, phenylethyl, $C_{7\text{-}19}$-alkylaryl, tolyl, 2,3-, 2,4-, 2,5-, 2,6-, 3,4- or 3,5-dimethylphenyl;

$R^6$ is selected from methyl, ethyl, n-propyl, isopropyl, n-, sec- and t-butyl, isobutyl, cyclopropyl, cyclobutyl, cyclopentyl, cyclohexyl, phenyl, benzyl, phenylethyl, $C_{7\text{-}19}$-alkylaryl, tolyl, 2,3-, 2,4-, 2,5-, 2,6-, 3,4- or 3,5-dimethylphenyl or $R^4$ and $R^6$ form a piperidine or morpholine ring together with the nitrogen atom to which they are attached;

$R^7$ and $R^8$ are each independently selected from H, methyl, ethyl, n-propyl, isopropyl, n-, sec- and t-butyl, isobutyl, pentyl, hexyl, cyclopropyl, cyclobutyl, cyclopentyl, cyclohexyl, phenyl, benzyl, phenylethyl, $C_{7\text{-}19}$-alkylaryl, tolyl, 2,3-, 2,4-, 2,5-, 2,6-, 3,4- or 3,5-dimethylphenyl or $R^7$ and $R^8$ form a five- or six-membered ring.

Particular preference is given to a process according to the invention in which the definitions of the residues of the compounds of the formulae (Ia), (Ib), (II), (III) and (IV) are defined as follows:

$R^1$ and $R^3$ are each independently selected from trifluoromethyl, difluoromethyl, difluorochloromethyl, pentafluoroethyl;

$R^2$ is selected from H, F, Cl, Br, COOH, $COOCH_3$, CN;

Z is selected from O, S, N—$R^4$;

$R^4$ is selected from methyl, ethyl, n-propyl, isopropyl, n-, sec- and t-butyl, isobutyl, cyclopropyl, phenyl, benzyl, tolyl;

$R^6$ is selected from methyl, ethyl, n-propyl, isopropyl, n-, sec- and t-butyl, isobutyl, cyclopropyl, phenyl, benzyl, tolyl or $R^4$ and $R^6$ form a piperidine or morpholine ring together with the nitrogen atom to which they are attached;

$R^7$ and $R^8$ are each independently selected from H, methyl, ethyl, n-propyl, isopropyl, n-, sec- and t-butyl, isobutyl, cyclopropyl, phenyl, benzyl, tolyl or $R^7$ and $R^8$ form a five- or six-membered ring.

Very particular preference is given to a process according to the invention in which the definitions of the residues of the compounds of the formulae (Ia), (Ib), (II), (III) and (IV) are defined as follows:

$R^1$ and $R^3$ are each independently selected from $CF_2H$ and $CF_3$, $R^2$ is H, Z is O, $R^6$ is selected from methyl or ethyl, $R^7$ and $R^8$ are each independently selected from H, methyl, phenyl.

Particular preference is given to a process according to the invention in which the definitions of the residues of the compounds of the formulae (Ia), (Ib), (II), (III) and (IV) are defined as follows:

$R^1$ and $R^3$ are each independently selected from $CF_2H$ and $CF_3$, $R^2$ is H, Z is O, $R^6$ is selected from methyl or ethyl, $R^7$ and $R^8$ are phenyl.

General Definitions

In the context of the present invention, the term halogens (Hal), unless defined otherwise, comprises those elements which are selected from the group comprising fluorine, chlorine, bromine and iodine, preferably fluorine, chlorine and bromine, more preferably fluorine and chlorine.

Optionally substituted groups may be mono- or polysubstituted, where the substituents in the case of polysubstitutions may be the same or different.

Haloalkyl: straight-chain or branched alkyl groups having 1 to 6 and preferably 1 to 3 carbon atoms (as specified above), where some or all of the hydrogen atoms in these groups may be replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent, for example haloalkylaminoalkyl etc., unless defined elsewhere. Preference is given to alkyl groups substituted by one or more halogen atoms, for example trifluoromethyl ($CF_3$), difluoromethyl ($CHF_2$), $CF_3CH_2$, $CF_2Cl$ or $CF_3CCl_2$.

Alkyl groups in the context of the present invention, unless defined otherwise, are linear, branched or cyclic saturated hydrocarbyl groups. The definition $C_1$-$C_{12}$-alkyl encompasses the widest range defined herein for an alkyl group. Specifically, this definition encompasses, for example, the meanings of methyl, ethyl, n-propyl, isopropyl, n-, sec- and t-butyl, isobutyl, n-pentyl, n-hexyl, 1,3-dimethylbutyl, 3,3-dimethylbutyl, n-heptyl, n-nonyl, n-decyl, n-undecyl or n-dodecyl.

Cycloalkyl: monocyclic, saturated hydrocarbyl groups having 3 to 8 and preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

Aryl groups in the context of the present invention, unless defined otherwise, are aromatic hydrocarbyl groups. The definition $C_{6\text{-}18}$-aryl encompasses the widest range defined herein for an aryl group having 6 to 18 atoms in the skeleton.

Specifically, this definition encompasses, for example, the meanings of phenyl, cycloheptatrienyl, cyclooctatetraenyl, naphthyl and anthracenyl.

Arylalkyl groups (aralkyl groups) in the context of the present invention, unless defined otherwise, are alkyl groups having a $C_{1-8}$-alkylene chain substituted by aryl groups. The definition $C_{7-19}$-aralkyl group encompasses the widest range defined herein for an arylalkyl group having a total of 7 to 19 atoms in the skeleton and alkylene chain. Specifically, this definition encompasses, for example, the meanings of benzyl and phenylethyl.

Alkylaryl groups (alkaryl groups) in the context of the present invention, unless defined otherwise, are aryl groups having a $C_{1-8}$-alkylene chain substituted by alkyl groups. The definition $C_{7-19}$-alkylaryl group encompasses the widest range defined herein for an alkylaryl group having a total of 7 to 19 atoms in the skeleton and alkylene chain. Specifically, this definition encompasses, for example, the meanings of tolyl or 2,3-, 2,4-, 2,5-, 2,6-, 3,4- or 3,5-dimethylphenyl.

The term intermediate used in the context of the present invention describes the substances which occur in the method according to the invention and are prepared for further chemical processing and are consumed or used therein in order to be converted to another substance. The intermediates can often be isolated and intermediately stored or are used without prior isolation in the subsequent reaction step. The term intermediate also encompasses the generally unstable and short-lived intermediates which occur transiently in multistage reactions (stage reactions) and to which local minima in the energy profile of the reaction process can be assigned.

The inventive compounds may be present as mixtures of any different isomeric forms possible, especially of stereoisomers, for example E and Z isomers, threo and erythro isomers, and optical isomers, but if appropriate also of tautomers. Both the E and the Z isomers are disclosed and claimed, as are the threo and erythro isomers, and also the optical isomers, any mixtures of these isomers, and also the possible tautomeric forms and salts thereof.

The present invention also provides intermediates of the formula (IV) and also salts thereof

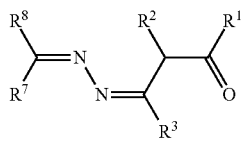

(IV)

in which
$R^1$ and $R^3$ are each independently selected from $C_1$-$C_6$-haloalkyl;
$R^2$ is selected from H, F, Cl, Br, COOH, (C=O)OR$^4$, CN and (C=O)NR$^4$R$^5$;
$R^4$ and $R^5$ are each independently selected from $C_{1-12}$-alkyl, $C_{3-8}$-cycloalkyl, $C_{6-18}$-aryl, $C_{7-19}$-arylalkyl or $C_{7-19}$-alkylaryl or
$R^4$ and $R^5$ form a five- or six-membered ring together with the nitrogen atom to which they are attached;
$R^7$ and $R^8$ are each independently selected from H, $C_{3-8}$-cycloalkyl, $C_{6-18}$-aryl, $C_{7-19}$-arylalkyl or $C_{7-19}$-alkylaryl or
$R^7$ and $R^8$ form a five- or six-membered ring.

In a preferred embodiment of the present invention, the residues in formula (IV) are defined as follows:
$R^1$ and $R^3$ are each independently selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl;
$R^2$ is selected from H, Cl, COOH, COOCH$_3$, COOC$_2$H$_5$, COOC$_3$H$_7$, CN and CONCH$_3$, CON(C$_2$H$_5$)$_2$;
$R^7$ and $R^8$ are each independently selected from H, methyl, ethyl, n-propyl, isopropyl, n-, sec- and t-butyl, isobutyl, pentyl, hexyl, cyclopropyl, cyclobutyl, cyclopentyl, cyclohexyl, phenyl, benzyl, phenylethyl, $C_{7-19}$-alkylaryl, tolyl, 2,3-, 2,4-, 2,5-, 2,6-, 3,4- or 3,5-dimethylphenyl or
$R^7$ and $R^8$ form a five- or six-membered ring.

In a particularly preferred embodiment of the present invention, the residues in formula (IV) are defined as follows:
$R^1$ and $R^3$ are each independently selected from trifluoromethyl, difluoromethyl, difluorochloromethyl, pentafluoroethyl;
$R^2$ is selected from H, F, Cl, Br, COOH, COOCH$_3$, CN;
$R^7$ and $R^8$ are each independently selected from H, methyl, ethyl, n-propyl, isopropyl, n, sec- and t-butyl, isobutyl, cyclopropyl, phenyl, benzyl, tolyl or wherein $R^7$ and $R^8$ may form a five- or six-membered ring.

In a very particularly preferred embodiment of the present invention, the residues in formula (IV) are defined as follows:
$R^1$ and $R^3$ are each independently selected from CF$_2$H and CF$_3$,
$R^2$ is H,
$R^7$ and $R^8$ are each independently selected from H, methyl, phenyl.

The present invention also provides intermediates of the formula (III) and also salts thereof,

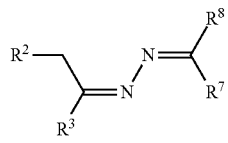

(III)

in which
$R^3$ is selected from $C_1$-$C_6$-haloalkyl;
$R^2$ is selected from H, F, Cl, Br, COOH, (C=O)OR$^4$, CN and (C=O)NR$^4$R$^5$;
$R^4$ and $R^5$ are each independently selected from $C_{1-12}$-alkyl, $C_{3-8}$-cycloalkyl, $C_{6-18}$-aryl, $C_{7-19}$-arylalkyl or $C_{7-19}$-alkylaryl or
$R^4$ and $R^5$ form a five- or six-membered ring together with the nitrogen atom to which they are attached;
$R^7$ and $R^8$ are each independently selected from H, $C_{1-12}$-alkyl, $C_{3-8}$-cycloalkyl, $C_{6-18}$-aryl, $C_{7-19}$-arylalkyl or $C_{7-19}$-alkylaryl or
$R^7$ and $R^8$ form a four-, five- or six-membered ring.

In a preferred embodiment of the present invention, the residues in formula (III) are defined as follows:
$R^3$ is selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2- difluoroethyl, 2,2-dichloro-2-fluoroethyl, 2,2,2-trichloroethyl, pentafluoroethyl and 1,1,1-trifluoroprop-2-yl;

$R^2$ is selected from H, Cl, COOH, COOCH$_3$, COOEt, COOC$_3$H$_7$, CN and CONMe$_2$, CONEt$_2$;

$R^7$ and $R^8$ are each independently selected from H, methyl, ethyl, n-propyl, isopropyl, n-, sec- and t-butyl, isobutyl, pentyl, hexyl, cyclopropyl, cyclobutyl, cyclopentyl, cyclohexyl, phenyl, $R^7$ and $R^8$ form a five- or six-membered ring.

In a particularly preferred embodiment of the present invention, the residues in formula (III) are defined as follows:

$R^3$ is selected from trifluoromethyl, difluoromethyl, difluorochloromethyl, pentafluoroethyl;

$R^2$ is selected from H, F, Cl, Br, COOH, COOMe, CN;

$R^7$ and $R^8$ are each independently selected from H, methyl, ethyl, n-propyl, isopropyl, n-, sec- and t-butyl, isobutyl, cyclopropyl, phenyl, benzyl, tolyl or $R^7$ and $R^8$ form a five- or six-membered ring.

In a very particularly preferred embodiment of the present invention, the residues in formula (III) are defined as follows:

$R^3$ is each independently selected from CF$_2$H and CF$_3$,
$R^2$ is H,
$R^7$ and $R^8$ are each independently selected from H, methyl, phenyl.

Particular preference is given to the following residues in formula (III):
$R^3$ is each independently selected from CF$_2$H and CF$_3$,
$R^2$ is H,
$R^7$ and $R^8$ are each independently selected from phenyl.

Method Description

Scheme 1:

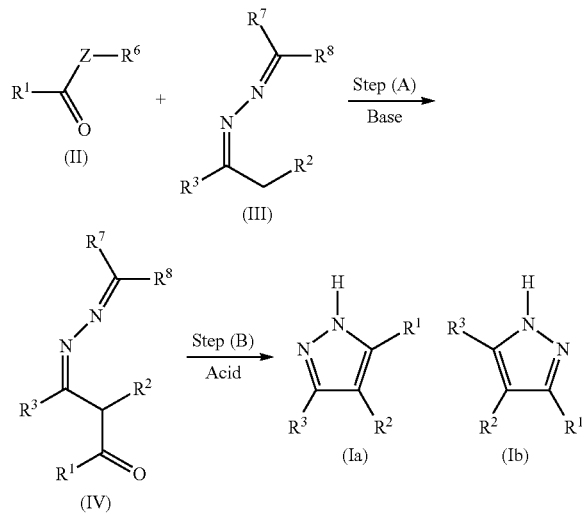

Step (A)

In step (A), fluoroalkyl esters, thioesters or amides of the formula (II) are reacted with hydrazones or azines of the formula (III) in the presence of a base to give compounds of the formula (IV) (Scheme 1). Compounds of the general formula (II) are preferably ethyl difluoroacetate, ethyl trifluoroacetate, ethyl difluorochloroacetate, N,N-dimethyltrifluoroacetamide. The compounds are commercially available. The compounds of the formula (III) are novel and can be prepared from ketones (V), (where $R^2$ and $R^3$ are as defined above) and hydrazines or hydrazones (VI), (where $R^7$ and $R^8$ are as defined above) according to Scheme 2.

Scheme 2:

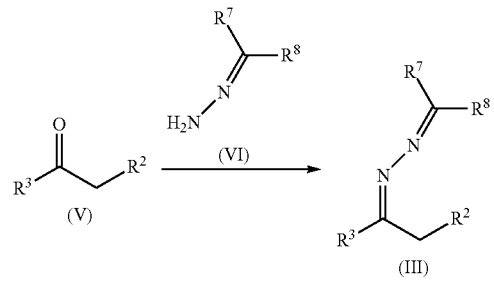

The reaction of the compounds of the formula (V) and preparation of (III) takes place at temperatures of −20° C. to +70° C., preferably at temperatures of −10° C. to +70° C., particularly preferably at 0° C. to 50° C. and atmospheric pressure (Scheme 2).

1 mole of the compounds of the formula (V) is reacted with 0.8 to 2 mol, preferably 0.9 to 1.5 mol, particularly preferably 1 to 1.5 mol of the compound of the formula (VI). A ratio of 1:1 of (V) to (VI) is particularly preferred.

The reaction time is not critical and may, according to the batch size and temperature, be selected within a range between a few minutes and several hours.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone, sulphoxides such as dimethyl sulphoxide or sulphones such as sulpholane, alcohols such as methanol, ethanol, isopropanol. Particular preference is given, for example, to THF, acetonitrile, ethers, toluene, chlorobenzene, n-hexane, cyclohexane or methylcyclohexane, ethanol, and very particular preference, for example, to acetonitrile, THF, methyl tert-butyl ether or ethanol The reaction of the compounds of the formulae (II) and (III) and preparation of (IV) takes place at temperatures of −20° C. to +70° C., preferably at temperatures of −10° C. to +60° C., particularly preferably at 0° C. to 50° C. and atmospheric pressure (Scheme 1).

1 mole of the compounds of the formula (III) according to the invention is reacted with 0.8 to 3 mol, preferably 0.9 to 2 mol, particularly preferably 1 to 2 mol of the compound of the formula (II).

The reaction is effected in the presence of a base. Preference is given to organic bases such as trialkylamine, pyridine, alkylpyridine, phosphazene and 1,8-diazabicyclo[5.4.0]undecene (DBU); alkali metal hydroxides such as lithium, sodium or potassium hydroxide, alkali metal carbonate (Na$_2$CO$_3$, K$_2$CO$_3$) and alkoxides such as NaOMe, NaOEt, NaO$^t$Bu, KO$^t$Bu or KF, NaH, methyllithium, butyllithium, hexamethyldisilazane, lithium diisopropylamide (LDA) and particular preference to NaH, NaOMe, NaO$^t$Bu, KO$^t$Bu.

In the method according to the invention, 1 to 2 mol of the base are taken for the compound of the formula (III).

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone, sulphoxides such as dimethyl sulphoxide or sulphones such as sulpholane. Particular preference is given, for example, to THF, acetonitrile, ethers, toluene, chlorobenzene, n-hexane, cyclohexane or methylcyclohexane, and very particular preference, for example, to acetonitrile, THF, methyl tert-butyl ether. The compounds of the formula (IV) may advantageously be isolated in the form of salts, for example, as a sodium or potassium salt.

Step (B)

The cyclization step (B) is typically effected without change of solvent and isolation of the compound of the formula (IV). The compounds of the formula (IV) are cyclized in the presence of an acid.

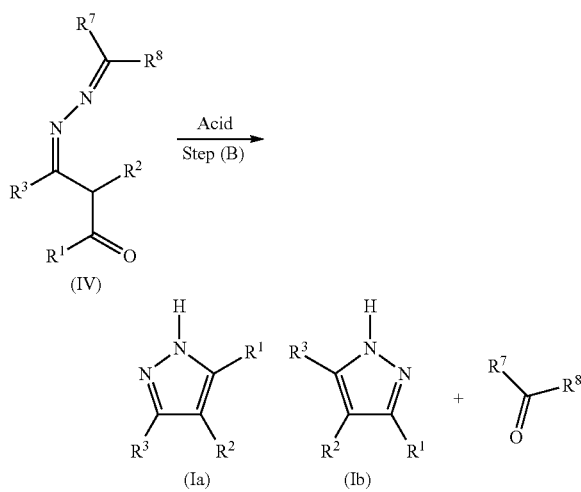

Preference is given to mineral acids, for example $H_2SO_4$, HCl, $HSO_3Cl$, HF, HBr, HI, $H_3PO_4$ or organic acids, for example $CF_3COOH$, p-toluenesulphonic acid, methanesulphonic acid, trifluoromethanesulphonic acid.

According to the invention, 0.1 to 2 mol, preferably 0.5 to 1.5 mol, of the acid are used per 1 mol of the compound of the formula (IV). If salts of the compounds of the formula (IV) are used in step (B), the acid is required to liberate a neutral compound from the salt. In the method according to the invention, the cyclization is effected at temperatures of −20° C. to +80° C., preferably at temperatures of −10° C. to +60° C., particularly preferably at −10° C. to 50° C. and atmospheric pressure. The reaction time is not critical and may, according to the batch size, be selected within a relatively wide range.

The ketones or aldehydes $R^7COR^8$ released may be reused in most cases.

Preference is given to performing all reaction steps of the method according to the invention in the same solvent and without isolation of the intermediates.

The compounds of the formula (I) ($R^2$ corresponds to $COOR^S$ or CN) can then be converted to pyrazole acids of the formula (I) ($R^2$ corresponds to COOH).

The inventive compounds (Ia) and (Ib) are used for the preparation of active fungicidal ingredients.

The method according to the invention is described further in the examples which follow. However, the examples should not be interpreted in a restrictive manner.

Characterisation of the Intermediate Compound:

Example 1

Potassium 4-[(diphenylmethylene)hydrazone]-1,1,5,5-tetrafluoropent-2-en-2-olate (IV-1)

To a mixture of 10.8 g (40 mmol) of 1-(1,1-difluoropropan-2-ylidene)-2-(diphenylmethylene)hydrazine and 10.2 g of ethyl difluoroacetate in 150 ml of methyl tert-butyl ether were added 9.06 g of potassium tert-butoxide over 1 hour and the mixture was stirred for 18 hours at 40° C. The mixture was cooled to 20° C., the precipitate was filtered off and washed with 10 ml of methyl tert-butyl ether. 13.1 g of product is obtained as a white solid.

$^{19}F$ δ: −119.35 (d, 2F, J=57 Hz), −120.65 (dd, 2F, J=56 Hz, 2 Hz.) ppm.

$^1$NMR δ: 7.6-7.40 (m, 1H), 7.36-7.40 (m, 2H), 7.60 (m, 2H), 7.36-7.40 (m, 1H), 7.36-7.40 (m, 2H), 7.24 (m, 2H), 7.79 (t, 1H), 5.17 (m, 1H), 5.75 (t, 1H) ppm.

$^{13}C$ δ: 114.9 (dt, 1H), 171.4 (t, 1H), 82.1 (d, 1H), 155.6 (t, 1H), 112.8 (dt, 1H), 156.1 (s, 1H), 140.4 (s, 1H), 130.4 (d, 2H), 128.1 (d, 2H), 128.8 (d, 1H), 136.8 (s, 1H), 128.7 (d, 2H), 128.6 (d, 2H), 129.2 (d, 1H) ppm.

Example 2

Potassium 4-[(diphenylmethylene)hydrazone]-1,1,1,5,5-pentafluoropent-2-en-2-olate (IV-2)

To a mixture of 11.6 g (40 mmol) of 1-(1,1,1-trifluoropropan-2-ylidene)-2-(diphenylmethylene)hydrazine and 10.2 g of ethyl difluoroacetate in 150 ml of methyl tert-butyl ether were added 9.06 g of potassium tert-butoxide over 1 hour and the mixture was stirred for 18 hours at 40° C. The mixture was cooled to 20° C., the precipitate was filtered off and washed with 10 ml of methyl tert-butyl ether. 13.4 g of product is obtained as a white solid.

Example 3

1-(Diphenylmethylene)-2-(1,1,1-trifluoropropan-2-ylidene)hydrazine (IV-3)

A mixture of benzophenone hydrazone (2 g, 10.2 mmol) and 1,1,1-trifluoroacetone (1.2 g, in 10 ml of ethanol) was stirred for 4 hours at 40° C. and the mixture was diluted with 100 ml of methyl tert-butyl ether. The organic phase was washed with water, dried over $MgSO_4$ and concentrated under reduced pressure. The product is a yellow oil (2.93 g, 98%).

$^1$NMR δ: 7.69-7.63 (m, 2H), 7.47-7.33 (m, 6H), 7.21-7.13 (m, 2H), 2.08 (s, 3H) ppm.

$^{13}C$ δ: 159.8, 148.2 (q, $J_{C-F}$=34 Hz), 137.2, 134.0, 132.4, 130.5, 129.5, 128.9, 128.3, 128.1, 120.4 (q, $J_{C-F}$=276 Hz), 12.8.

$^{19}F$ δ: −72.3 (s, 3F).

Example 4

1-(1,1-Difluoropropan-2-ylidene)-2-(diphenylmethylene)hydrazine (IV-4)

A mixture of (320 g, 1.63 mol) benzophenone hydrazone and (153 g, 1.63 mol) 1,1-difluoroacetone in 3 L of ethanol was stirred for 3 hours at 40° C.

80 g of NaHCO3 were added to the mixture and the suspension was stirred for 1 hour and filtered. The filtrate was concentrated under reduced pressure. 444 g of yellow oil was obtained with a purity of 94-95%. Yield (93-95%).

$^1$NMR δ: 7.70-7.62 (m, 2H), 7.46-7.30 (m, 6H), 7.20-7.10 (m, 2H), 5.92 (t, 1H, J=56 Hz), 2.04 (s, 3H).

$^{13}$C δ: 160.1, 154.5 (t, $J_{C-F}$=32 Hz), 137.4, 134.4, 132.4, 130.4, 129.3, 128.8, 128.3, 128.1, 114.4 (t, $J_{C-F}$=239 Hz), 11.0.

$^{19}$F δ: −120.1 (d, 2F, J=55 Hz).

Example 5

Ethyl 3-[(diphenylmethylene)hydrazinylidene]-4,4-difluorobutanoate (IV-5)

A mixture of (1.96 g, 10 mmol) benzophenone hydrazone and (1.73 g, 10 mmol) ethyl 4,4-difluoro-3-oxobutanoate in 20 ml of ethanol was stirred for 5 hours at 40° C. and the mixture was concentrated under reduced pressure. A solid is obtained with a melting point of 122° C. to 123° C. (3.26 g, 95%).

$^1$NMR δ: 7.70-7.3 (m, 10 H), 7.22 (t, 1H, J=56 Hz), 3.85 (q, 2H), 1.85 (s, 2H), 1.2 (t, 3H) ppm.

M/Z=344.

Characterisation of the End Products:

Example 6

3,5-Bis(difluoromethyl)pyrazole (Ia/b-1)

34.8 g (0.1 mol) of potassium 4-[(diphenylmethylene)hydrazone]-1,1,5,5-tetrafluoropent-2-en-2-olate were dissolved in 100 ml of water and 20 ml of HCl (d 1.19) were then added to adjust the pH of the solution to 1. The mixture was stirred for 3 hours at 50° C. and the product was extracted with 300 ml of methyl tert-butyl ether. The organic phase was washed with water, dried over MgSO4 and concentrated under reduced pressure. The residue was distilled under a reduced pressure of 15 mbar. The fraction having a boiling point of 135° C. to 145° C./15 mbar was collected. The oil crystallizes. 16 g (96%) of product is obtained with m.p. of 70-72° C.

$^1$ NMR (400 MHz, CDCl$_3$): 12.5 (br, 1H), 6.77 (t, 2H, J=54.8 Hz), 6.74 (s, 1H).

$^{13}$C δ: 142.9, 109.3 (t, $J_{C-F}$=236 Hz), 103.2.

$^{19}$F δ: −113.2 (d, 4F, J=54.4 Hz).

Example 7

3-Trifluoromethyl-5-difluoromethylpyrazole (Ia/b-2)

Prepared from potassium 4-[(diphenylmethylene)hydrazone]-1,1,1,5,5-pentafluoropent-2-en-2-olate as described in example 6.

A solid is obtained.

$^1$NMR δ: 12.6 (br, 1H), 6.81 (s, 1H), 6.76 (t, 1H, J=54.5 Hz) ppm.

$^{13}$C δ: 140.7, 128.8, 120.3 (q, $J_{C-F}$=266 Hz), 108.5 (t, $J_{C-F}$=237 Hz), 103.8 ppm.

$^{19}$F δ: −61.7 (s, 3F), −112.9 (d, 2F, J=54.7 Hz) ppm.

Example 8

Ethyl 3,5-bis(difluoromethyl)-1H-pyrazole-4-carboxylate (Ia/b-3)

To a mixture of (3.44 g, 10 mmol) ethyl 3-[(diphenylmethylene)hydrazinylidene]-4,4-difluorobutanoate and 1.02 g of ethyl difluoroacetate in 15 ml of methyl tert-butyl ether are added 1 g of potassium tert-butoxide and the mixture is stirred for 18 hours at 40° C. The mixture is cooled to 20° C., the precipitate is filtered off and dissolved in 15 ml of ethanol 2 ml of HCl were added to the solution and the mixture is stirred for 3 hours at 50° C. The product is extracted with 50 ml of methyl tert-butyl ether. The organic phase is washed with water, dried over MgSO4 and concentrated under reduced pressure. The residue is purified by means of column chromatography (ethyl acetate/methylcyclohexane).

1.87 g (78%) of product is obtained.

$^1$NMR δ: 7.15 (t, 2h, CHF$_2$, $J_{H-F}$=53.6 Hz), 4.39 (q, 2H, CH$_2$, J=7.1 Hz), 1.39 (t, 3H, CH$_3$, J=7.1 Hz) ppm.

$^{13}$C NMR δ: 161.1 (CO), 143.8 (t, $C_{IV}$ arom, $J_{C-F}$=23.1 Hz), 111.6 ($C_{IV}$ arom), 108.2 (t, $J_{C-F}$=238.4 Hz), 61.7 (CH$_2$), 13.9 (CH$_3$) ppm.

$^{19}$F NMR δ: −117.3 (CHF$_2$, $J_{F-H}$=53.6 Hz) ppm.

Example 9

3,5-Bis(difluoromethyl)-1H-pyrazole-4-carboxylate (Ia/b-4)

2.4 g of ethyl 3,5-bis(difluoromethyl)-1H-pyrazole-4-carboxylate are dissolved in 10 ml of ethanol and slowly admixed with an 8 N aqueous sodium hydroxide solution (3 ml) and the mixture stirred for 2 hours at room temperature. The solvent is removed, the residue is taken up in water (10 ml) and extracted with diethyl ether (10 ml). After acidifying to pH 1 with 6M HCl, the product is extracted with diethyl ether. The organic phase is dried over sodium sulphate, filtered and the solvent is removed. 3,5-Difluoromethyl-4-pyrazolecarboxylic acid (2 g) are isolated as a colourless solid.

$^1$H NMR (CDCl$_3$) δ: 7.18 (t, 2H, CHF$_2$, $J_{H-F}$=53.6 Hz) ppm.

The invention claimed is:

1. Method for preparing a 3,5-bis(fluoroalkyl)pyrazole derivative of formula (Ia) and/or (Ib),

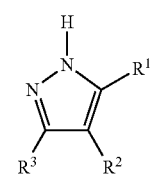

(Ia)

-continued

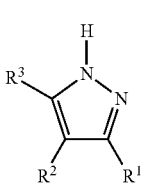
(Ib)

in which
$R^1$ and $R^3$ are each independently selected from $C_1$-$C_6$-haloalkyl;
$R^2$ is selected from H, F, Cl, Br, COOH, (C=O)O$R^4$, CN and (C=O)N$R^4R^5$;
$R^4$ and $R^5$ are each independently selected from $C_{1-12}$-alkyl, $C_{3-8}$-cycloalkyl, $C_{6-18}$-aryl, $C_{7-19}$-arylalkyl or $C_{7-19}$-alkylaryl or
$R^4$ and $R^5$ may form a five- or six-membered ring together with the nitrogen atom to which they are attached;
comprising reacting in (A) one or more fluoroalkyl esters, thioesters or amides of formula (II),

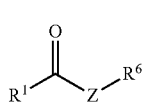
(II)

in which
Z is selected from O, S, N—$R^4$;
$R^4$ is as defined above;
$R^6$ is selected from $C_{1-12}$-alkyl, $C_{3-8}$-cycloalkyl, $C_{6-18}$-aryl, $C_{7-19}$-arylalkyl or $C_{7-19}$-alkylaryl or
$R^4$ and $R^6$ may form a five- or six-membered ring together with the nitrogen atom to which they are attached;
$R^1$ is as defined above;
with one or more compounds of formula (III),

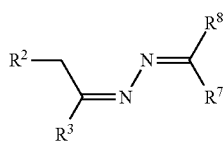
(III)

in which the residues $R^2$, $R^3$, $R^4$ and $R^5$ are as defined above,
and $R^7$ and $R^8$ are each independently selected from H, $C_{1-12}$-alkyl, $C_{3-8}$-cycloalkyl, $C_{6-18}$-aryl, $C_{7-19}$-arylalkyl or $C_{7-19}$-alkylaryl,
or $R^7$ and $R^8$ may form a four-, five- or six-membered ring;
in the presence of a base to give one or more compounds of formula (IV)

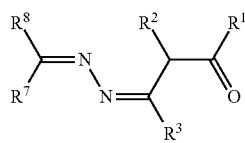
(IV)

and which are then cyclized in (B) in the presence of an acid to give one or more compounds of formula (Ia) and (M).

2. Method according to claim 1, wherein
$R^1$ and $R^3$ are each independently selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl;
$R^2$ is selected from H, Cl, COOH, COOCH$_3$, COOC$_2$H$_5$, COOC$_3$H$_7$, CN and CON(CH$_3$)$_2$, CONC$_3$H$_7$;
Z is selected from O, S, N—$R^4$;
$R^4$ is selected from methyl, ethyl, n-propyl, isopropyl, n-, sec- and t-butyl, isobutyl, cyclopropyl, cyclobutyl, cyclopentyl, cyclohexyl, phenyl, benzyl, phenylethyl, $C_{7-19}$-alkylaryl, tolyl, 2,3-, 2,4-, 2,5-, 2,6-, 3,4- or 3,5-dimethylphenyl;
$R^6$ is selected from methyl, ethyl, n-propyl, isopropyl, n-, sec- and t-butyl, isobutyl, cyclopropyl, cyclobutyl, cyclopentyl, cyclohexyl, phenyl, benzyl, phenylethyl, $C_{7-19}$-alkylaryl, tolyl, 2,3-, 2,4-, 2,5-, 2,6-, 3,4- or 3,5-dimethylphenyl or
$R^4$ and $R^6$ form a piperidine or morpholine ring together with the nitrogen atom to which they are attached;
$R^7$ and $R^8$ are each independently selected from H, methyl, ethyl, n-propyl, isopropyl, n-, sec- and t-butyl, isobutyl, pentyl, hexyl, cyclopropyl, cyclobutyl, cyclopentyl, cyclohexyl, phenyl, benzyl, phenylethyl, $C_{7-19}$-alkylaryl, tolyl, 2,3-, 2,4-, 2,5-, 2,6-, 3,4- or 3,5-dimethylphenyl or
$R^7$ and $R^8$ form a five- or six-membered ring.

3. Method according to claim 1, wherein
$R^1$ and $R^3$ are each independently selected from trifluoromethyl, difluoromethyl, difluorochloromethyl, pentafluoroethyl;
$R^2$ is selected from H, F, Cl, Br, COOH, COOCH$_3$, CN;
Z is selected from O, S, N—$R^4$;
$R^4$ is selected from methyl, ethyl, n-propyl, isopropyl, n-, sec- and t-butyl, isobutyl, cyclopropyl, phenyl, benzyl, tolyl;
$R^6$ is selected from methyl, ethyl, n-propyl, isopropyl, n-, sec- and t-butyl, isobutyl, cyclopropyl, phenyl, benzyl, tolyl or
$R^4$ and $R^6$ form a piperidine or morpholine ring together with the nitrogen atom to which they are attached;
$R^7$ and $R^8$ are each independently selected from H, methyl, ethyl, n-propyl, isopropyl, n-, sec- and t-butyl, isobutyl, cyclopropyl, phenyl, benzyl, tolyl or $R^7$ and $R^8$ form a five- or six-membered ring.

4. Method according to claim 1, wherein
$R^1$ and $R^3$ are each independently selected from CF$_2$H and CF$_3$,
$R^2$ is H,
Z is O,
$R^6$ is selected from methyl or ethyl,
$R^7$ and $R^8$ are each independently selected from H, methyl, phenyl.

5. Method according to claim 1, wherein
$R^1$ and $R^3$ are each independently selected from CF$_2$H and CF$_3$,
$R^2$ is H,
Z is O,
$R^6$ is selected from methyl or ethyl,
$R^7$ and $R^8$ are phenyl.

6. Compound of formula (IV),

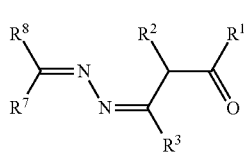

in which
R¹ and R³ are each independently selected from $C_1$-$C_6$-haloalkyl;
R² is selected from H, F, Cl, Br, COOH, (C=O)OR⁴, CN and (C=O)NR⁴R⁵;
R⁴ and R⁵ are each independently selected from $C_{1-12}$-alkyl, $C_{3-8}$-cycloalkyl, $C_{6-18}$-aryl, $C_{7-19}$-arylalkyl or $C_{7-19}$-alkylaryl or
R⁴ and R⁵ form a five- or six-membered ring together with the nitrogen atom to which they are attached;
R⁷ and R⁸ are each independently selected from H, $C_{1-12}$-alkyl, $C_{3-8}$-cycloalkyl, $C_{6-18}$-aryl, $C_{7-19}$-arylalkyl or $C_{7-19}$-alkylaryl or
R⁷ and R⁸ form a five- or six-membered ring.

7. Compound of formula (IV) according to claim 6, in which
R¹ and R³ are each independently selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl;
R² is selected from H, Cl, COOH, COOCH₃, COOC₂H₅, COOC₃H₇, CN and CONCHS, CON(C₂H₅)₂;
R⁷ and R⁸ are each independently selected from H, methyl, ethyl, n-propyl, isopropyl, n-, sec- and t-butyl, isobutyl, pentyl, hexyl, cyclopropyl, cyclobutyl, cyclopentyl, cyclohexyl, phenyl, benzyl, phenylethyl, $C_{7-19}$-alkylaryl, tolyl, 2,3-, 2,4-, 2,5-, 2,6-, 3,4- or 3,5-dimethylphenyl or
R⁷ and R⁸ form a five- or six-membered ring.

8. Compound of formula (IV) according to claim 6, in which
R¹ and R³ are each independently selected from trifluoromethyl, difluoromethyl, difluorochloromethyl, pentafluoroethyl;
R² is selected from H, F, Cl, Br, COOH, COOCH₃, CN;
R⁷ and R⁸ are each independently selected from H, methyl, ethyl, n-propyl, isopropyl, n, sec- and t-butyl, isobutyl, cyclopropyl, phenyl, benzyl, tolyl or wherein R⁷ and R⁸ may form a five- or six-membered ring.

9. Compound of formula (IV) according to claim 6, in which
R¹ and R³ are each independently selected from CF₂H and CF₃,
R² is H,
R⁷ and R⁸ are each independently selected from H, methyl, phenyl.

10. Compound of formula (III),

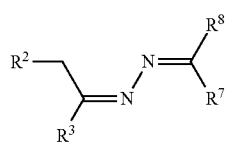

in which
R³ is selected from $C_1$-$C_6$-haloalkyl;
R² is selected from H, F, Cl, Br, COOH, (C=O)OR⁴, CN and (C=O)NR⁴R⁵;
R⁴ and R⁵ are each independently selected from $C_{1-12}$-alkyl, $C_{3-8}$-cycloalkyl, $C_{6-18}$-aryl, $C_{7-19}$-arylalkyl or $C_{7-19}$-alkylaryl or
R⁴ and R⁵ form a five- or six-membered ring together with the nitrogen atom to which they are attached;
R⁷ and R⁸ are each independently selected from H, $C_{1-12}$-alkyl, $C_{3-8}$-cycloalkyl, $C_{6-18}$-aryl, $C_{7-19}$-arylalkyl or $C_{7-19}$-alkylaryl, wherein R⁷ and R⁸ are not both methyl, or
R⁷ and R⁸ form a four-, five- or six-membered ring.

11. Compound of formula (III) according to claim 10, wherein
R³ is selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl;
R² is selected from H, Cl, COOH, COOCH₃, COOEt, COOC₃H₇, CN and CONMe₂, CONEt₂;
R⁷ and R⁸ are each independently selected from H, methyl, ethyl, n-propyl, isopropyl, n-, sec- and t-butyl, isobutyl, pentyl, hexyl, cyclopropyl, cyclobutyl, cyclopentyl, cyclohexyl, phenyl, benzyl, phenylethyl, $C_{7-19}$-alkylaryl, tolyl, 2,3-, 2,4-, 2,5-, 2,6-, 3,4- or 3,5-dimethylphenyl wherein R⁷ and R⁸ are not both methyl, or
R⁷ and R⁸ form a five- or six-membered ring.

12. Compound of formula (III) according to claim 10, in which
R³ is selected from trifluoromethyl, difluoromethyl, difluorochloromethyl, pentafluoroethyl;
R² is selected from H, F, Cl, Br, COOH, COOMe, CN;
R⁷ and R⁸ are each independently selected from H, methyl, ethyl, n-propyl, isopropyl, n-, sec- and t-butyl, isobutyl, cyclopropyl, phenyl, benzyl, tolyl, wherein R⁷ and R⁸ are not both methyl, or
R⁷ and R⁸ form a five- or six-membered ring.

13. Compound of formula (III) according to claim 10, in which
R³ is each independently selected from CF₂H and CF₃,
R² is H,
R⁷ and R⁸ are each independently selected from phenyl.

14. A process for preparing one or more active fungicidal ingredients, comprising a method according to claim 1.

* * * * *